(12) United States Patent
Yamamoto et al.

(10) Patent No.: US 8,013,182 B2
(45) Date of Patent: Sep. 6, 2011

(54) CARBOXYLIC ACID ESTER, USE OF THE SAME, AND METHOD FOR PRODUCING THE SAME

(75) Inventors: Yoshihiro Yamamoto, Settsu (JP); Tatsuya Ohtsuka, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/734,606

(22) PCT Filed: Nov. 6, 2008

(86) PCT No.: PCT/JP2008/070164
§ 371 (c)(1),
(2), (4) Date: May 12, 2010

(87) PCT Pub. No.: WO2009/063783
PCT Pub. Date: May 22, 2009

(65) Prior Publication Data
US 2010/0234634 A1 Sep. 16, 2010

(30) Foreign Application Priority Data
Nov. 13, 2007 (JP) ................. 2007-294050

(51) Int. Cl.
*C07C 69/66* (2006.01)
*C07C 43/00* (2006.01)

(52) U.S. Cl. ........................ 560/184; 568/683

(58) Field of Classification Search .......... None
See application file for complete search history.

(56) References Cited

U.S. PATENT DOCUMENTS

| | | | |
|---|---|---|---|
| 3,321,515 A | 5/1967 | Moore et al. | |
| 3,544,633 A | 12/1970 | Yodis et al. | |
| 3,683,092 A | 8/1972 | Regan et al. | |
| 4,250,334 A | 2/1981 | Coon et al. | |
| 4,885,398 A | 12/1989 | Sonoi et al. | |
| 4,960,947 A | 10/1990 | Sonoi et al. | |
| 5,466,879 A | 11/1995 | Cheburkov | |
| RE35,568 E * | 7/1997 | Halpern et al. | 568/683 |
| 5,811,596 A | 9/1998 | Kawai et al. | |
| 5,969,193 A | 10/1999 | Terrell | |
| 5,990,359 A | 11/1999 | Ryan et al. | |
| 6,100,434 A | 8/2000 | Bieniarz et al. | |
| 6,469,219 B1 | 10/2002 | Khrimian et al. | |
| 7,598,425 B2 | 10/2009 | Yamamoto et al. | |
| 2008/0262273 A1 | 10/2008 | Yamamoto et al. | |

FOREIGN PATENT DOCUMENTS

| | | | |
|---|---|---|---|
| JP | 61-25694 | | 6/1986 |
| JP | 61-277645 | | 12/1986 |
| JP | 01-203339 | | 8/1989 |
| JP | 06-184025 | | 7/1994 |
| JP | 11-116521 | | 4/1999 |
| JP | 2002-234860 | | 8/2002 |
| JP | 2002234860 | * | 8/2002 |
| JP | 2005-306747 | | 11/2005 |
| WO | 97/30961 | | 8/1997 |

OTHER PUBLICATIONS

International Search Report issued Dec. 9, 2008 in International (PCT) Application No. PCT/JP2008/070164.

* cited by examiner

*Primary Examiner* — Paul A Zucker
(74) *Attorney, Agent, or Firm* — Wenderoth, Lind & Ponack, L.L.P.

(57) ABSTRACT

The present invention provides a process for producing a novel compound, i.e., α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms, comprising reacting an α-methoxycarboxylic acid ester represented by General Formula (2): $(CF_3)_2C(OCH_3)COOR$, wherein R is as defined above, with molecular chlorine; and a process for producing 1,1,1,3,3,3-hexafluoroisopropyl fluoromethyl ether represented by a chemical formula $(CF_3)_2CH(OCH_2F)$, comprising fluorinating and decarboxylating the α-chloromethoxycarboxylic acid ester.

According to the present invention, 1,1,1,3,3,3-hexafluoroisopropyl fluoromethyl ether (sevoflurane), which is known as a compound having an anesthetic property, can be produced efficiently and at a low cost.

4 Claims, No Drawings

US 8,013,182 B2

CARBOXYLIC ACID ESTER, USE OF THE SAME, AND METHOD FOR PRODUCING THE SAME

TECHNICAL FIELD

The present invention relates to a novel α-chloromethoxycarboxylic acid ester that is useful as an intermediate of sevoflurane, a process for producing the same, and a process for producing sevoflurane using the α-chloromethoxycarboxylic acid ester.

BACKGROUND ART 1,1,1,3,3,3-hexafluoro-2-methoxypropane, represented by the chemical formula: $(CF_3)_2CH(OCH_3)$, is a material that is useful as a starting material for anesthetic sevoflurane (see Patent Documents 1, 2, etc., listed below). The production of sevoflurane at a low cost is an important issue, and various methods have been contemplated hitherto.

For example, Patent Document 1 listed below discloses a method wherein 1,1,1,3,3,3-hexafluoro-2-propyl methyl ether, which is obtained by methylation of hexafluoroisopropanol (HFIP), is reacted with chlorine gas to produce 1,1,1,3,3,3-hexafluoro-2-propyl chloromethyl ether, and this resulting compound is then reacted with KF in an organic solvent to produce sevoflurane; a method wherein 1,1,1,3,3,3-hexafluoro-2-propyl methyl ether is reacted with $BrF_3$; and a method wherein HFIP is reacted with hydrogen fluoride and formaldehyde.

However, the above-described reaction in which the chloromethyl ether is fluorinated with KF has the drawback of requiring a high temperature and prolonged reaction, and thus poses problems for implementation on an industrial scale. The method wherein the methyl ether is reacted with $BrF_3$ requires handling $BrF_3$, which is dangerous, and is therefore not suitable for mass production. The method wherein HFIP is reacted with hydrogen fluoride and formaldehyde suffers from a low yield that is due to the formation of a polyether as a by-product.

To overcome these problems, Patent Document 3 listed below, for example, discloses a method wherein hydrogen fluoride and paraformaldehyde are reacted with HFIP in the presence of sulfuric acid. Moreover, Patent Document 2 listed below discloses a method wherein the methyl ether of HFIP is reacted with chlorine gas to produce 1,1,1,3,3,3-hexafluoro-2-propyl chloromethyl ether, which is then reacted with hydrogen fluoride and amine.

With respect to the method wherein hydrogen fluoride and paraformaldehyde are reacted with HFIP in the presence of sulfuric acid, the following inventions have been made as methods for further improving the yield.

For example, Patent Document 4 listed below discloses a process wherein a polyether compound formed as a by-product during the reaction is reacted with hydrogen fluoride and a reaction accelerator such as sulfuric acid or the like to produce sevoflurane. Patent Document 5 listed below discloses a process wherein hydrogen fluoride and paraformaldehyde are reacted with HFIP in the presence of sulfuric acid, and the formed sevoflurane is separated from the mixture at equilibrium by distillation or extraction, thereby increasing the yield.

Moreover, Patent Document 6 discloses a process wherein HFIP is reacted with bis(fluoromethyl)ether in the presence of an acid.

In addition to the above-described processes, a number of processes for producing sevoflurane are known, and most of these processes use HFIP as a starting material. As a process for producing HFIP, a process wherein hexafluoroacetone or its hydrate is reduced by hydrogen in the presence of a catalyst (see Patent Documents 7, 8, etc., listed below) is known. As processes for producing hexafluoroacetone, a process wherein hexafluoropropylene oxide is rearranged in the presence of a catalyst (Patent Document 9), and a process wherein hexachloroacetone is fluorinated with hydrogen fluoride (Patent Document 10) are known. The former process, however, has a problem in that the starting material, i.e., hexafluoropropylene oxide, is expensive. The latter process also has problems in that the purification methods for separating the resulting hexafluoroacetone from hydrochloric acid, for separating the byproduct chlorofluoroacetone, and the like are complicated, making the process costly.

In view of these circumstances, attempts have been made to produce hexafluoroacetone at a low cost. Processes that are attracting attention, in particular, are those using, as starting materials, $(CF_3)_2CHCF_2OCH_3$ (2H-octafluoroisobutyl methyl ether; hereinafter abbreviated to "OIME") obtained by reacting methanol with octafluoroisobutene, i.e., a by-product of hexafluoropropene that is mass-produced as a monomer for fluororesins; $(CF_3)_2C=CFOCH_3$ (heptafluoroisobutenyl methyl ether; hereinafter abbreviated to "HIME") obtained by removing HF from OIME; and the like.

Patent Document 11, for example, discloses a process for producing hexafluoroacetone hydrate, wherein HIME is reacted with oxygen under photoradiation.

Patent Document 12 discloses a process for producing hexafluoroacetone or its hydrate, wherein OIME or HIME is reacted with oxygen in the presence of an activated carbon catalyst.

Patent Document 13 discloses a process for producing hexafluoroacetone, wherein OIME is reacted with triethylamine to produce hexafluoroacetone oxime, which is then hydrolyzed with acid.

Patent Document 14 discloses a process for producing hexafluoroacetone hydrate, wherein $(CF_3)_2C(OH)CO_2CH_3$ (methyl 3,3,3-trifluoro-2-trifluoromethyl-2-hydroxypropionate; hereinafter abbreviated to "MTTHP") is hydrolyzed and then decarboxylated by reacting the hydrolyzed product with a halogenating agent.

The process utilizing photo-oxidation of HIME, however, has problems in that it is difficult to industrially perform photoradiation, and that the yield is low. The oxidation process that uses an activated carbon catalyst has problems, such as the inability to perform a long-term operation due to the significant degradation of the catalyst, low selectivity of hexafluoroacetone, and the like. In addition, the process wherein OIME is reacted with triethylamine to produce an oxime has a problem in that triethylamine, which is an auxiliary starting material, is expensive. The process wherein MTTHP is hydrolyzed and then decarboxylated by halogenation uses an inexpensive auxiliary starting material and has a high yield, but it has the drawback of requiring a large number of steps.

Processes for producing HFIP at a low cost without using hexafluoroacetone as an intermediate have been examined as follows.

For example, Patent Document 15 discloses a process for producing HFIP, comprising synthesizing MTTHP by oxidation of HIME, hydrolyzing the resulting MTTHP, and decarboxylating the hydrolyzed product in the presence of a protic solvent. However, after the present inventors recreated the experiment, this process was found to result in a low yield because of the formation of $CF_3(HCF_2)C=O$ (pentafluoroacetone) as a by-product during decarboxylation.

As described above, although the low-cost production of hexafluoroacetone or HFIP is an important issue, satisfactory results have yet to be obtained.

Accordingly, in order to produce sevoflurane at a low cost, there is a strong desire for the development of a process for producing hexafluoroacetone or HFIP at a low cost, or the development of a process for producing sevoflurane without using these intermediates.

Patent Document 1: U.S. Pat. No. 3,683,092
Patent Document 2: Japanese Unexamined Patent Publication No. H11-116521
Patent Document 3: U.S. Pat. No. 4,250,334
Patent Document 4: WO 97/30961
Patent Document 5: U.S. Pat. No. 6,469,21
Patent Document 6: U.S. Pat. No. 5,990,359
Patent Document 7: Japanese Examined Patent Publication No. S61-25694
Patent Document 8: Japanese Unexamined Patent Publication No. H6-184025
Patent Document 9: U.S. Pat. No. 3,321,515
Patent Document 10: U.S. Pat. No. 3,544,633
Patent Document 11: Japanese Unexamined Patent Publication No. S61-277645
Patent Document 12: Japanese Unexamined Patent Publication No. H1-203339
Patent Document 13: U.S. Pat. No. 5,466,879
Patent Document 14: Japanese Unexamined Patent Publication No. 2005-306747
Patent Document 15: Japanese Unexamined Patent Publication 2002-234860

DISCLOSURE OF THE INVENTION

Object to be Achieved by the Invention

The present invention was made in view of the above-described current status of the prior art. A primary object of the present invention is to provide a process capable of efficient and low-cost production of 1,1,1,3,3,3-hexafluoroisopropyl fluoromethyl ether (sevoflurane), which is known as a compound that has anesthetic properties, and a novel compound useful in the production of the aforementioned compound.

Means to Achieve the Object

The present inventors have carried out extensive research to achieve the above-mentioned object. As a result, they have found that a novel compound, α-chloromethoxycarboxylic acid ester, can be produced by using a known compound, 3,3,3-trifluoro-2-trifluoromethyl-2-methoxypropionic acid ester, as a starting material, and reacting the methoxy group with chlorine. Further, the present inventors found that, when reacting the α-chloromethoxycarboxylic acid ester with alkali metal fluorides as a fluorinating agent, the decarboxylation reaction proceeds along with the halogen exchange reaction, and the desired 1,1,1,3,3,3-hexafluoroisopropyl fluoromethyl ether (sevoflurane) can be efficiently produced by a relatively simple process. The present inventors completed the present invention based on these findings.

In other words, the present invention provides the following α-chloromethoxycarboxylic acid ester, a process for producing the same, and a process for producing 1,1,1,3,3,3-hexafluoroisopropyl fluoromethyl ether (sevoflurane) from the α-chloromethoxycarboxylic acid ester.

1. An α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms.

2. A process for producing 1,1,1,3,3,3-hexafluoroisopropyl fluoromethyl ether represented by the chemical formula $(CF_3)_2CH(OCH_2F)$, comprising fluorinating and decarboxylating an α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms.

3. The process for producing 1,1,1,3,3,3-hexafluoroisopropyl fluoromethyl ether as defined in Item 2, comprising reacting an α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms, with a fluorinating agent represented by the chemical formula $MF \cdot (HF)_n$, wherein M is H, Na, K, or Cs, and n is 0 or 1.

4. A process for producing an α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms, comprising reacting an α-methoxycarboxylic acid ester represented by General Formula (2): $(CF_3)_2C(OCH_3)COOR$, wherein R is as defined above, with molecular chlorine.

Below, a novel α-chloromethoxycarboxylic acid ester that is useful as an intermediate of 1,1,1,3,3,3-hexafluoroisopropyl fluoromethyl ether and a process for producing the same are first described, and then a process for producing 1,1,1,3,3,3-hexafluoroisopropyl fluoromethyl ether from the α-chloromethoxycarboxylic acid ester is described.

Novel α-Chloromethoxycarboxylic Acid Ester and Process for Producing the Same

According to the present invention, an α-chloromethoxycarboxylic acid ester represented by General Formula (1): $(CF_3)_2C(OCH_2Cl)COOR$, wherein R is a hydrocarbon group which may be substituted with at least one atom selected from the group consisting of halogen, oxygen, nitrogen, and sulfur atoms, can be obtained by reacting an α-methoxycarboxylic acid ester represented by General Formula (2): $(CF_3)_2C(OCH_3)COOR$, wherein R is as defined above, with molecular chlorine.

In the α-methoxycarboxylic acid ester represented by General Formula (2): $(CF_3)_2C(OCH_3)COOR$, which is used as a starting material, a hydrocarbon group represented by R may be $C_1$-$C_{10}$ alkyl, aryl, aralkyl, and the like.

Of these groups, the alkyl is preferably methyl, ethyl, isopropyl, t-butyl, hexyl, or the like. The aryl is preferably phenyl, naphthyl, pyridyl, chlorophenyl, or the like. The aralkyl is preferably benzyl, phenethyl, or the like. Among these, methyl is particularly preferable because of its low production cost.

Note that the α-methoxycarboxylic acid ester represented by General Formula (2): $(CF_3)_2C(OCH_3)COOR$ can be produced by using, as a starting material, a hydroxy carboxylic acid ester represented by General Formula (3): $(CF_3)_2C(OH)COOR$, wherein R is as defined above, which is a known compound disclosed in Japanese Unexamined Patent Application No. 2002-234860 and the like, and carrying out the conventional methylation of a hydroxyl group in which, for example, the hydroxy group is converted to alkoxide using a hydroxide of alkali metals (Li, K, Na, etc.) and then reacted with a methylating agent such as dimethyl sulfate.

According to the present invention, an α-chloromethoxycarboxylic acid ester represented by General Formula (1): $(CF_3)_2C(OCH_2Cl)COOR$ can be obtained by reacting the α-methoxycarboxylic acid ester represented by the above-described General Formula (2) with molecular chlorine and thereby chlorinating the methyl ether group in the α-methoxycarboxylic acid ester.

On the other hand, for example, according to a process for chloromethylating a hydroxyl group using aluminum chloride and trioxane disclosed in U.S. Pat. No. 6,100,434, when the α-hydroxycarboxylic acid ester represented by the above-described General Formula (3): $(CF_3)_2C(OH)COOR$ was used as a starting material, generation of the desired chloromethylated product was not observed and only the starting material was recovered.

However, research by the present inventors showed that, when the α-methoxycarboxylic acid ester represented by the above-described General Formula (2): $(CF_3)_2C(OCH_3)COOR$ is reacted with molecular chlorine, the chlorination of the methyl ether group proceeds quickly, and an α-chloromethylated product can be obtained.

Although the reaction between the α-methoxycarboxylic acid ester represented by General Formula (2) and molecular chlorine can be carried out by application of heat or addition of various radical reaction initiators, it is particularly preferable to carry out the reaction by the use of light irradiation whose reaction conditions can be easily controlled.

The reaction under light irradiation can be performed by, for example, bubbling chlorine through the starting material.

The amount of chlorine used is preferably about 0.1 to 1.7 equivalents, more preferably 0.7 to 1.2 equivalents, per equivalent of α-methoxycarboxylic acid ester represented by General Formula (2): $(CF_3)_2C(OCH_3)COOR$.

The above reaction can be carried out in the presence or absence of a solvent. When a solvent is used, it is preferable to use a solvent, such as carbon tetrachloride, chloroform, tetrachloroethylene, acetic acid, carbon disulfide, etc., that is relatively stable to chlorine.

The reaction temperature is usually about 0° C. to about 100° C., preferably about 10° C. to about 50° C.

The reaction time is determined by the flow rate of chlorine. Because the temperature in the reaction system increases as the flow rate of chlorine is increased, the reaction time needs to be suitably set, taking into account the condition of heat removal.

The conditions of light irradiation are not particularly limited. For example, the reaction may be carried out under light irradiation using a mercury lamp with a spectral range of 200 nm to 600 nm. Besides a mercury lamp, the light irradiation may also be performed using, for example, a tungsten-halogen lamp, a xenon lamp, mercury-xenon lamp, and the like.

The α-chloromethoxycarboxylic acid ester represented by General Formula (1): $(CF_3)_2C(OCH_2Cl)COOR$, which is obtained by the above-described process, is a novel compound undisclosed in literature, and can be efficiently converted to 1,1,1,3,3,3-hexafluoroisopropyl methyl ether (sevoflurane) by a process described below. Accordingly, α-chloromethoxycarboxylic acid ester is a compound that is useful as an intermediate of sevoflurane.

Process for Producing
1,1,1,3,3,3-Hexafluoroisopropyl Fluoromethyl Ether
(Sevoflurane)

According to the present invention, 1,1,1,3,3,3-hexafluoroisopropyl fluoromethyl ether (sevoflurane) represented by the chemical formula $(CF_3)_2CH(OCH_2F)$ can be obtained by subjecting the α-chloromethoxycarboxylic acid ester represented by the above-described General Formula(1): $(CF_3)_2C(OCH_2Cl)COOR$, wherein R is as defined above, to a halogen exchange reaction and a decarboxylation reaction.

With the aim of developing a method for synthesizing sevoflurane, the present inventors attempted to synthesize 1,1,1,3,3,3-hexafluoroisopropyl chloromethyl ether (sevochlorane), which is a precursor of sevoflurane, by hydrolyzing and decarboxylating the α-chloromethoxycarboxylic acid ester represented by the above General Formula (1). However, the hydrolysis of a chloromethyl ether moiety proceeded along with alkaline hydrolysis of an ester group, and the generation of sevochlorane was not observed.

However, in an attempt to synthesize an α-fluoromethoxycarboxylic acid ester represented by General Formula (4): $(CF_3)_2C(OCH_2F)COOR$, wherein R is as defined above, by a normal halogen exchange reaction using, as a starting material, the α-chloromethoxycarboxylic acid ester represented by the above-described General Formula (1): $(CF_3)_2C(OCH_2Cl)COOR$, the present inventors unexpectedly found that the decarboxylation proceeds simultaneously under the conditions of a halogen exchange reaction and that 1,1,1,3,3,3-hexafluoroisopropyl fluoromethyl ether (sevoflurane) represented by the chemical formula $(CF_3)_2CH(OCH_2F)$ can be obtained.

The above-described halogen exchange reaction and decarboxylation reaction can be carried out by reacting the α-chloromethoxycarboxylic acid ester represented by General Formula (1) with a fluorinating agent represented by the chemical formula $MF \cdot (HF)_n$, wherein M is H, Na, K, or Cs, and n is 0 or 1.

Specific examples of fluorinating agents represented by the chemical formula $MF \cdot (HF)_n$ include hydrogen fluoride, sodium fluoride, potassium fluoride, cesium fluoride, potassium hydrogen fluoride ($KHF_2$), sodium hydrogen fluoride ($NaHF_2$), and the like. These fluorinating agents can be used alone or in a combination of two or more.

The amount of the fluorinating agent used is about 0.2 to about 10 equivalents, preferably about 1 to about 5 equivalents, more preferably about 1 to about 3 equivalents, per equivalent of α-chloromethoxycarboxylic acid ester represented by General Formula (1).

Solvents with a high dielectric constant are preferably used as reaction solvents, and examples of such reaction solvents that can be suitably used include glycol solvents such as ethylene glycol, polyethylene glycol, and the like; glyme solvents such as diglyme, triglyme, and the like; amide solvents such as N,N-dimethylformamide, N-methylpyrrolidone, and the like; nitrile solvents such as acetonitrile, propionitrile, and the like; ketone solvents such as acetone, methyl ethyl ketone, methyl isobutyl ketone, and the like; sulfoxide solvents such as dimethyl sulfoxide, and the like; and sulfone solvents such as sulfolane, and the like.

These organic solvents can be used alone or in a combination of two or more.

The reaction temperature is usually from about 0° C. to about 200° C., preferably about 20° C. to about 150° C., more preferably about 50° C. to about 100° C.

The reaction time is usually from about 10 minutes to about 24 hours, preferably about 1 hour to about 10 hours.

The 1,1,1,3,3,3-hexafluoroisopropyl fluoromethyl ether (sevoflurane) obtained by the above-described process can be isolated and purified by a known method, for example, distillation, extraction, etc.

Advantageous Effects

According to the present invention, a novel substance, α-chloromethoxycarboxylic acid ester represented by General Formula (1), which is useful as an intermediate of an anesthetic agent, i.e., sevoflurane (1,1,1,3,3,3-hexafluoroisopropyl fluoromethyl ether), can be obtained at a high yield using a known substance, hydroxy carboxylic acid ester represented by General Formula (3), as a starting material.

Further, the α-chloromethoxycarboxylic acid ester can be efficiently converted to sevoflurane by the halogen exchange reaction and the decarboxylation reaction.

Thus, the present invention can produce sevoflurane efficiently and at a low cost, using a known substance, α-hydroxycarboxylic acid ester, as a starting material.

BEST MODE FOR CARRYING OUT THE INVENTION

Below, the present invention is described in detail with reference to the examples.

EXAMPLE 1

Methyl 3,3,3-trifluoro-2-trifluoromethyl-2-methoxypropionate (100 g, 417 mmol) and carbon tetrachloride (100 g) were added to a flask for photoreaction, and then chlorine gas (10 to 20 ml/min) was slowly blown thereinto over 5 hours under water cooling, stirring, and irradiation with a high-pressure mercury lamp, with the internal temperature being 30° C. or below.

After blowing was completed, the resulting crude product was washed with water, and distilled under normal pressure. Methyl 3,3,3-trifluoro-2-trifluoromethyl-2-chloromethoxypropionate (41.3 g) was recovered as a fraction having a boiling point of 125° C. to 135° C. (bath temperature: 165° C. to 175° C.) (GC conversion rate: 37%).

$^1$H-NMR(CDCl$_3$: TMS standard) δ 4.0 ppm (s, 3H), 5.7 ppm (s, 2H)
$^{19}$F-NMR(CDCl$_3$: CFCl$_3$ standard) δ −71.6 ppm (s, 6F)
MS(EI): m/z(%)=239(21), 159(35), 69(55), 59(100), 45(89), 15(48).

COMPARATIVE EXAMPLE 1

Methyl 3,3,3-trifluoro-2-trifluoromethyl-2-hydroxypropionate (10 g, 44.25 mmol), CH$_2$Cl$_2$ (50 ml), and AlCl$_3$ (5.9 g, 44.25 mmol) were added to a 100 ml 3-neck flask, and then trioxane (1.35 g, 15 mmol) was added thereto under room temperature and stirring.

After the addition, the mixture was stirred for about 1 hour at room temperature, and the reaction temperature was increased to 50° C. The reaction was further continued for 4 hours and then finished.

The reaction solution was added to 6N aqueous HCl solution, and then separated and condensed. Thereby a crude product (10 g) was recovered.

As a result of GC-mass analysis of the recovered product, the desired chloromethoxylated product was absent, and only the starting material was recovered.

Note that the recovered product contained the chlorination products of trioxane (Cl—CH$_2$—O—CH$_2$—Cl, etc.).

EXAMPLE 2

Methyl 3,3,3-trifluoro-2-trifluoromethyl-2-chloromethoxypropionate (4.06 g, 14.8 mmol), KF (2.5 g, 43 mmol) and polyethyleneglycol (PEG-400) (15 g) having an average molecular weight of 380 to 420 were added to a 50 ml flask, and then the reaction was carried out for about 5 hours under heating at 90° C. to 95° C. and stirring.

The result of GC-mass analysis and $^{19}$F-NMR quantitative analysis (CF$_3$CH$_2$OH internal standard) of the recovered product confirmed that sevoflurane was obtained in a 45.4% yield from methyl 3,3,3-trifluoro-2-trifluoromethyl-2-chloromethoxypropionate, which was used as a starting material.

EXAMPLE 3

Methyl 3,3,3-trifluoro-2-trifluoromethyl-2-chloromethoxypropionate (2.0 g, 7.3 mmol), KF (1.0 g, 17.2 mmol, and polyethyleneglycol (PEG-400) (5 g) having an average molecular weight of 380 to 420 were added to a 50 ml autoclave made of SUS, and then the reaction was carried out for about 5 hours under heating at 90° C. to 95° C. and stirring.

The result of GC-mass analysis and $^{19}$F-NMR quantitative analysis (CF$_3$CH$_2$OH internal standard) of the recovered product confirmed that sevoflurane was obtained in a 51.7% yield from methyl 3,3,3-trifluoro-2-trifluoromethyl-2-chloromethoxypropionate, which was used as a starting material.

REFERENCE EXAMPLE 1

Methyl 3,3,3-trifluoro-2-trifluoromethyl-2-chloromethoxypropionate (8.9 g, 32.42 mmol), MeOH (12 g, 375 mmol) and 20% aqueous NaOH solution (5.2 g, 37.5 mmol) were added to a 100 ml 3-neck flask, and then the reaction was carried out under room temperature and stirring.

The GC analysis found that the ester remained even at a stage where the pH of the reaction solution became neutral. Thus, 20% aqueous NaOH solution (3 g, 21.6 mmol) was further added to the solution, and the reaction was carried out until the ester was no longer present. Then, the reaction was finished.

The result of NMR analysis of the reaction solution confirmed the absence of a —CH$_2$Cl group and the production of sodium 3,3,3-trifluoro-2-trifluoromethyl-2-hydroxypropionate.

The invention claimed is:

1. An α-chloromethoxycarboxylic acid ester represented by General Formula (1): (CF$_3$)$_2$C(OCH$_2$Cl)COOR, wherein R is a hydrocarbon group which may be substituted with at least one atom selected from the group consisting of halogen, oxygen, nitrogen, and sulfur atoms.

2. A process for producing 1,1,1,3,3,3-hexafluoroisopropyl fluoromethyl ether represented by the chemical formula: (CF$_3$)$_2$CH(OCH$_2$F), comprising fluorinating and decarboxylating an α-chloromethoxycarboxylic acid ester represented by General Formula (1): (CF$_3$)$_2$C(OCH$_2$Cl)COOR, wherein R is a hydrocarbon group which may be substituted with at least one atom selected from the group consisting of halogen, oxygen, nitrogen, and sulfur atoms.

3. The process for producing 1,1,1,3,3,3-hexafluoroisopropyl fluoromethyl ether as defined in claim 2, comprising reacting an α-chloromethoxycarboxylic acid ester represented by General Formula (1): (CF$_3$)$_2$C(OCH$_2$Cl)COOR, wherein R is a hydrocarbon group which may be substituted with at least one atom selected from the group consisting of halogen, oxygen, nitrogen, and sulfur atoms, with a fluorinating agent represented by the chemical formula MF·(HF)$_n$, wherein M is H, Na, K, or Cs, and n is 0 or 1.

4. A process for producing an α-chloromethoxycarboxylic acid ester represented by General Formula (1):
(CF$_3$)$_2$C(OCH$_2$Cl)COOR, wherein R is a hydrocarbon group which may be substituted with at least one atom selected from the group consisting of halogen, oxygen, nitrogen, and sulfur atoms, comprising reacting an α-methoxycarboxylic acid ester represented by General Formula (2): (CF$_3$)$_2$C(OCH$_3$)COOR, wherein R is as defined above, with molecular chlorine.

* * * * *